(12) United States Patent
Vicinay et al.

(10) Patent No.: US 7,537,909 B2
(45) Date of Patent: May 26, 2009

(54) ENZYMATIC METHOD OF PRODUCING 4-O-β-D-GALACTOPYRANOSYL-D-XYLOSE, 4-O-β-D-GALACTOPYRANOSYL-D-XYLOSE OBTAINED USING SAID METHOD, COMPOSITIONS CONTAIN SAME AND THE USE THEREOF IN EVALUATING INTESTINAL LACTASE

(75) Inventors: Francisco Javier Cañada Vicinay, Madrid (ES); Guillerno Corrales Morales, Madrid (ES); Alfonso Fernández-Mayoralas Alvarez, Madrid (ES); Manuel Martín Lomas, Seville (ES); Juan José Aragón Reyes, Madrid (ES)

(73) Assignees: Consejo Superior de Investigaciones Cientificas, Madrid (ES); Universidad Autonoma de Madrid, Madrid (ES)

( * ) Notice: Subject to any disclaimer, the term of this patent is extended or adjusted under 35 U.S.C. 154(b) by 425 days.

(21) Appl. No.: 10/738,378

(22) Filed: Dec. 17, 2003

(65) Prior Publication Data

US 2004/0241811 A1 Dec. 2, 2004

Related U.S. Application Data

(63) Continuation of application No. PCT/ES02/00297, filed on Jun. 14, 2002.

(30) Foreign Application Priority Data

Jun. 18, 2001 (ES) .............................. 200101419

(51) Int. Cl.
*C12Q 1/54* (2006.01)
*C12Q 1/34* (2006.01)
*C12P 19/14* (2006.01)
*C12P 19/12* (2006.01)

(52) U.S. Cl. ............................ 435/14; 435/18; 435/99; 435/100

(58) Field of Classification Search ....................... None
See application file for complete search history.

(56) References Cited

U.S. PATENT DOCUMENTS 4,228,274 A * 10/1980 Ponpipom et al. .......... 536/17.9
4,675,392 A * 6/1987 Dahmen et al. ............ 536/17.6
5,770,405 A * 6/1998 Wong-Madden et al. ...... 435/74
5,994,092 A * 11/1999 Aragon Reyes et al. ....... 435/14

OTHER PUBLICATIONS

Rivera-Sagredo et al., "4-O-β-D-galactopyranosyl-D-xylose: A New Synthesis and application to the evaluation of intestinal lactase" Carbohydrate Research, vol. 228(1) 1992, pp. 129-135.*
M. J. Crumpton and D. A. L. Davies "The Isolation of D-Fucosamine from the Specific Polysaccharide of *Chromobacterium violaceum* (NCTC 7917)" Biochem J. 70(4) 1958, p. 729.*
Rao et al. "Carbohydrate Composition of Finger Millet (*Eleusine coracana*) and Foxtail Millet (*Setaria italica*)" CarboQual. Plant-Pl. Fds.hum. Nutr. XXVIII, 4: 1979, p. 293.*
Fujimoto et al. "Purification and properties of recombinant B-galactosidase from *Bacillus circulans*" Glycogonjugate Journal 15, p. 155, 1998.*
Gabelsberger et al "Cloning and characterization of B-glactoside and B-glucoside hydrolysing enzymes of *Thermotoga maritima*" FEMS Letters, 109(2-3), p. 131, 1993.*
Shinji Yoshitake, Yoshitsugu Yamada, Eiji Ishikawa, and Rene Masseyeff "Conjugation of Glucose Oxidase from *Aspergillus niger* and Rabbit Antibodies Using N-Hydroxysuccinimide Ester of N-(4-Carboxycyclohexylmethyl)-Maleimide" Eur. J. Biochem. 101, 395-399 (1979).*
Peter H. Schippers and Harry P. J. M. Dekkers "Direct Determination of Absolute Circular Dichroism Data and Calibration of Commercial Instruments" Anal. Chem. 1981, 53, 778-782.*
Lopez et al, Enzymatic beta-galactosidation of beta-xylopyranosides, Biotechnol. Lett., vol. 13, n° 10, 1991, pp. 705-710.
Gorin et al, The Synthesis of Beta-Galacto- and Beta-Gluco-Pyranosyl Disaccharides by *Sporobolomyces singularis*, Jun. 1, 1964.
Aragon, J.J. et al, Evaluation of rat intestinal lactase in vivo with 4-galactosylxylose, Clinica Chimica Acta, vol. 210, Sep. 30, 1992, Amsterdam, NL, pp. 221-226.

* cited by examiner

*Primary Examiner*—L Blaine Lankford
*Assistant Examiner*—Thane Underdahl
(74) *Attorney, Agent, or Firm*—Klauber & Jackson, LLC

(57) ABSTRACT

An enzymatic process to obtain 4-O-β-D-galactopyranosyl-D-xylose useful in compositions or solutions in the in vivo evaluation of intestinal lactose activity in humans, that comprises the steps of preparing a reaction mixture of D-xylose, a β-D-galactopyranoside and a reaction medium that comprises water buffered to a pH between 5.0 and 9.0; adding 10 to 1,000 units of β-D-galactosidase per gram of β-D-galactopyranoside; subjecting the reaction mixture to a reaction or a temperature between a temperature higher than the freezing point of the reaction mixture and 45° C., for 2 to 48 hours; for the reaction by deactivation of the β-D-galactosidase; and to isolate and crystallize the fractions that contain 4-O-β-D-galactopyranosyl-D-xylose from a crystallization mixture selected between mixtures of acetone/methanol in a ratio between 5/1 to 20/1 and mixtures of acetone/water in a ratio between 5/1 to 20/1.

37 Claims, No Drawings

ENZYMATIC METHOD OF PRODUCING 4-O-β-D-GALACTOPYRANOSYL-D-XYLOSE, 4-O-β-D-GALACTOPYRANOSYL-D-XYLOSE OBTAINED USING SAID METHOD, COMPOSITIONS CONTAIN SAME AND THE USE THEREOF IN EVALUATING INTESTINAL LACTASE

RELATED APPLICATIONS

The present application is a Continuation of co-pending PCT Application No. PCT/ES02/00297, filed Jun. 14, 2002, which in turn, claims priority from Spanish Application Serial No. 200101419, filed Jun. 18, 2001. Applicants claim the benefits of 35 U.S.C. §120 as to the PCT application and priority under 35 U.S.C. §119 as to said Spanish application, and the entire disclosures of both applications are incorporated herein by reference in their entireties.

The present invention is comprised in the field of the process to obtain compounds, specifically disaccharides useful in bloodless evaluation methods of intestinal lactase activity.

BACKGROUND OF THE INVENTION

The deficiency or low intestinal lactase activity that results in insufficient capacity or up to the incapacity to digest lactase, is rare as a congenital metabolic error, but it is a common syndrome in human adults. However, in most mammals there is a noticeable reduction of lactase activity from the moment of weaning. In humans whose ancestors have depended on a substantial consumption of milk or milk products for a long time, this reduction is less frequent. On the other hand, in unweaned babies, deficient or low intestinal lactase activity is rather infrequent.

The determination of intestinal lactase activity is important in pediatrics and gastroenterology and it can be carried out directly, from a sample of mucous membrane, or indirectly, from the level of sugar in the blood or from exhaled hydrogen, after administering a dose of lactase to the individual.

Direct determination has the disadvantage of being a complex and expensive method due to the fact that it requires special instruments and very specialized staff in order to remove the sample that should be subjected to analysis afterwards, aside from the fact that it is unpleasant and somewhat dangerous for the individual.

Other methods to determine intestinal lactase are based on the fact that disaccharides are, based on their affinity to lactase, capable of acting as a lactase substrate and they are converted, by action of the enzyme, into certain monosaccharides that are easily absorbed by the intestine and excreted in urine.

Spanish patent ES-P-9001680 describes the preparation of 4-O-β-galactopyranosyl-D-xylose disaccharide of formula (I)

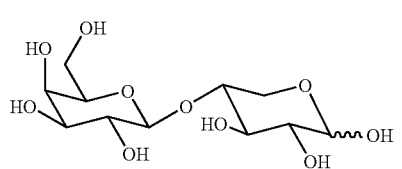

for the evaluation of intestinal lactase activity. Said disaccharide is administered orally, acts as a substrate of intestinal lactase and therefore it decomposes in the intestinal tract, into xylose and galactose, the xylose being absorbed and excreted in urine, wherein xylose can be evaluated directly by means of a simple calorimetric method.

The amounts of xylose excreted in urine are correlated with the levels of intestinal lactase.

Spanish patent ES-P-9001680 also describes a method for basically preparing 4-O-β-galactopyranosyl-D-xylose, that comprises synthesis of benzyl β-D-xylopyranoside and that follows a sequence of operations that implies selective protection, glycosilation and deprotection reactions. The number of steps of the reaction, as well as the use of expensive reagents such as silver triflate in the glycosilation reaction, and the use of chromatography columns in the purification of intermediates and of the final product, produce costs and have difficulties to carry out this process on an industrial scale.

Spanish patents ES-P-9502185 and ES-P-9701156 describe enzymatic processes for the preparation of mixtures of galactopyranosyl-xylose disaccharides that contain the disaccharide (I) and its regioisomers 2-O-β-D-galactopyranosyl-D-xylose and 3-O-β-D-galactopyranosyl-D-xylose that, respectively, have the following formulae:

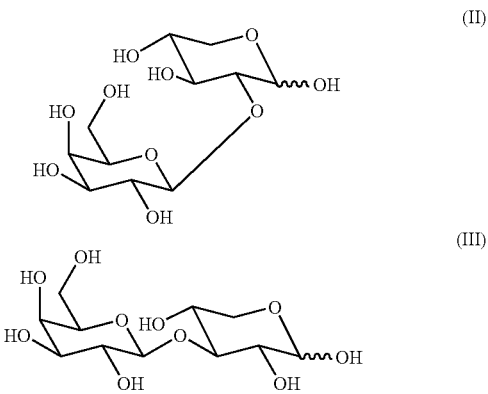

The processes described in Spanish patents ES-P-9502185 and ES-P-9701156 make it possible to obtain in a single reaction step and after chromatographic purification, mixtures of 2-, 3- and 4-O-β-D-galactopyranosyl-D-xylose useful as substrates and, therefore, for the determination of the enzymatic activity of intestinal lactase. Said processes, although feasible from accessible substrates and enzymes, have difficulties, from the point of view of industrial synthesis, for the characterization of the most suitable proportions, reproducibility of the preparation in said proportions and the determination of possible impurities.

On the other hand, Gorin et al. in "The Synthesis of β-Galacto- and β-Gluco-Pyranosyl Disaccharides by *Sporobolomyces Singularis*", Can. J. Chem. 42(1964) 2307-2319, describe the synthesis of a plurality of disaccharides, among them 2-O-β-D-galactopyranosyl-D-xylose and 3-O-β-D-galactopyranosyl-D-xylose, by means of a process using cells. This publication does not describe any use of the different synthesized disaccharides.

OBJECT OF THE INVENTION

The first object of the invention is to overcome the above-cited inconveniences of the prior art.

Another object of the invention is to provide an improved process that implies any enzymatic reaction between D-xylose and a β-D-galactopyranoside substrate and a subsequent phase of isolation and purification, that makes it possible to increase the proportion of 4-O-β-D-galactopyranosyl-D-xylose in the final mixture of the enzymatic reaction with respect to the 2- and 3-O-β-D-galactopyranosyl-D-xylose, from whose final mixture 4-O-β-D-galactopyranosyl-D-xylose can be isolated by simple operations.

The 4-O-β-D-galactopyranosyl-D-xylose that can be obtained by means of the above-cited process, as well as the compositions that comprise said 4-O-β-D-galactopyranosyl-D-xylose, constitute subsequent objects of the invention.

Another object of the invention is to use 4-O-β-D-galactopyranosyl-D-xylose in the preparation of compositions and solutions useful in the in vivo evaluation of intestinal lactase activity.

DESCRIPTION OF THE INVENTION

The above-cited objects are achieved in accordance with the present invention, by means of an enzymatic process to obtain 4-O-β-D-galactopyranosyl-D-xylose that comprises
a first step of preparation of a first reaction mixture of
2-20% by weight of D-xylose
0.5-5% by weight of a β-D-galactopyranoside substrate
75-97.5% by weight of a reaction medium that comprises buffered water at a pH between 5.0 and 9.0;
adding 10 to 1,000 units of a β-D-galactosidase enzyme, per gram of β-D-galactopyranoside to the first reaction mixture; and obtaining a second reaction mixture;
a second step wherein the second reaction mixture is subjected to a reaction at a temperature comprised between a temperature higher than the freezing point of the second reaction mixture and 45° C., for 2 to 48 hours, in order to form disaccharides in the second reaction mixture;
a third step wherein the reaction is stopped when the disaccharides have been formed in the desired amount, by means of a treatment chosen between deactivation of β-D-galactosidase by freezing the second reaction mixture at a temperature between 20° C. and −170° C., deactivation of β-D-galactosidase by heating the second reaction mixture at a temperature between 95 and 110° C., and separation of β-D-galactosidase from the second reaction mixture by ultrafiltration; obtaining a third reaction mixture;
a fourth step wherein an aglyconic fragment of the β-D-galactopyranoside substrate used in the first step is separated from the third reaction mixture by extraction or filtration; obtaining a fourth reaction mixture;
a fifth step comprising isolation of fractions that contain 4-O-β-D-galactopyranosyl-D-xylose, selected among adding celite to the fourth reaction mixture, followed by solid-liquid extraction with a solvent and elution with a first eluent in a column;
and directly adding active carbon to the fourth reaction mixture followed by filtration and elution with a second eluent,
and a sixth step, wherein the fractions that contain 4-O-β-D-galactopyranosyl-D-xylose are crystallized in a crystallization mixture selected among mixtures of acetone/methanol in a ratio between 5/1 and 20/1 and mixtures of acetone/water in a ratio between 5/1 and 20/1.

In accordance with the invention, the proportion of D-xylose in the second reaction mixture is preferably 7.5% by weight, the proportion of β-D-galactopyranoside in the second reaction mixture is 1.5% by weight, and 100 units of β-D-galactosidase per gram of β-D-galactopyranoside are added.

Optionally, the reaction medium may also comprise at least a cosolvent medium selected among dimethylsulfoxide, dimethylformamide, dioxane and mixtures thereof, preferably in a proportion of 20% as referred to the reaction medium. In an embodiment of the invention, the reaction medium is buffered to a pH of 7.

The reaction is conveniently carried out at a constant temperature for the purpose of increasing its reproducibility. In an embodiment of the process of the invention, the reaction temperature is higher than the freezing point of the second reaction mixture and is lower than 40° C. In another embodiment, the reaction is carried out at room temperature, which permits good yields without the need of cooling the second reaction mixture. The reaction may also be carried out at −5° C. or at 37° C. The reaction temperature is preferably lower than 0° C. but higher than the freezing point of the second reaction mixture.

In accordance with the invention, the β-D-galactopyranoside substrate is preferably selected among o-nitrophenyl β-D-galactopyranoside (Gal-ONP) and lactose. The β-galactosidase enzyme can be *E. coli* β-galactosidase or *Kluyveramyces lactis* β-galactosidase (such as for example MAXILACT®). When Gal-ONP is used as the substrate on-nitrophenol is formed in the reaction and the same is eliminated by extraction with ethyl acetate in the event that the reaction is stopped by heating, or else it is eliminated by simple filtration in the event that the reaction is stopped by cooling.

When, in the third step of the process the reaction is stopped by freezing the second reaction mixture, a temperature of −78° C. is preferably applied. On the other hand, when in the third step the reaction is stopped by heating the second reaction mixture, a temperature of 100° C. is preferably applied.

In the fifth step, the 4-O-β-D-galactopyranosyl-D-xylose may be isolated from the reaction mixture, by means of several alternative methods.

According to a first alternative method, water is eliminated from the fourth reaction mixture in order to obtain a reaction residue that contains disaccharides, the reaction residue is subjected to an acetylation treatment in order to obtain a peracetylated 4-O-β-D-galactopyranosyl-D-xylose derivative and to separation of the peracetylated derivative in a silica gel chromatographic column. Acetylation of the reaction residue is preferably carried out with acetic anhydride in pyridine, whereas, deacetlyation of the peracetylated derivative is carried out catalytically with sodium methoxide in methanol.

According to a second alternative method, the fourth reaction mixture is subjected to elution in a column with a first eluent that may be selected among mixtures of water with methanol, ethanol or isopropanol, preferably a mixture of water/isopropanol with a proportion of isopropanol of 1 to 10% (v/v), preferably 2% (v/v).

Elution is carried out in a filtration column selected among filtration columns with cross-linked dextrane polymer fillers, such as for example a column with SEPHADEX filler, filtration columns with acrylamide polymer fillers, such as for example, a column with BIOGEL filler, and filtration columns of active carbon or of active carbon-celite in order to obtain fractions that contain 4-O-β-D-galactopyranosyl-D-xylose.

Preferably, the fourth reaction mixture is concentrated before being subjected to elution in the column. According to a third alternative method, celite is added to the fourth reaction mixture, the mixture thus obtained is concentrated to dryness and the residue is subjected to solid-liquid extraction with an organic solvent in a Soxhlet extractor followed by elution in a column. The solvent preferred for the solid-liquid extraction is ethyl acetate. The column is selected among filtration columns with cross-linked dextrane polymer fillers, such as for example a column with SEPHADEX filler, filtration columns with acrylamide polymer fillers, such as for example a column with BIOGEL filler and filtration columns of active carbon or of active-carbon-celite. Preferably the column is of active carbon-celite, wherein the carbon is deactivated by adding hydrochloric acid.

This third alternative method offers the advantage of eliminating most of the xylose—above all when it is used in great excess in the reaction—before elution in the column whereby the fillers, as well as the amount of first eluent that is needed for elution is much less. Another advantage of this third alternative method is that the solid-liquid extraction in ethyl acetate is completely selective given that in the liquid phase no presence of disaccharides is observed, but rather only of xylose and galactose.

According to a fourth alternative method, elution in the fifth step is carried out by adding active carbon to the fourth reaction mixture instead of using a filler column, once the aglyconic fragment has been separated from the substrate in the fourth step, thus achieving that the 4-O-β-D-galactopyranosyl-D-xylose is adsorbed on the active carbon and eluting the 4-O-β-D-galactopyranosyl-D-xylose of the active carbon with a second eluent. Said elution is preferably carried out by means of consecutive washings with water and with diluted isopropanol with a growing proportion in volume of isopropanol in successive steps. The proportion in volume of isopropanol is comprised between 1% and 3% in a first step, between 3% and 5% in a second step, and between 5% and 7% in a third step. The concentration of isopropanol preferred for washing is a 2% isopropanol sequence, followed by elution with 4% isopropanol and followed by elution with 6% isopropanol. Pure 4-O-β-D-galactopyranosyl-D-xylose is obtained from the residue obtained, by concentration crystallizing it in acetone-water.

Preferably, according to this fourth alternative method o-nitrophenyl β-D-galactopyranoside is used as a substrate for the reaction.

According to this fourth alternative method, multiple advantages are obtained, such as the fact that it is not necessary to heat the second reaction mixture to 100° C. to stop the reaction, nor is it necessary to separate the aglyconic fragment from the substrate in the fourth step by means of extraction. Likewise, the need to concentrate the fourth reaction mixture is avoided, and hence, caramelization thereof is not produced. The amount of active carbon that would be needed for the filler of a column is reduced, the total amount of eluents is also reduced and the use of celite is avoided.

In accordance with the invention according to the sixth step the fractions that contain 4-O-β-D-galactopyranosyl-D-xylose obtained in a crystallization mixture selected among mixtures of acetone/methanol in a ratio between 5/1 and 20/1 and mixtures of acetone/water in a ratio between 5/1 and 20/1, preferably a ratio of 10/1, are crystallized.

The invention also refers to 4-O-β-D-galactopyranosyl-D-xylose obtained by the above-described method, and to compositions and saline or aqueous solutions that comprise a 4-O-β-D-galactopyranosyl-D-xylose obtained by means of said process, as well as use of a 4-O-β-D-galactopyranosyl-D-xylose in the preparation of compositions and solutions for in vivo evaluation of intestinal lactase in humans.

In such compositions and solutions, the β-D-galactopyranosyl-D-xylose is combined with pharmaceutically acceptable amounts of at least an additive selected from among pharmaceutically acceptable stabilizers, protecting agents, flavoring agents, lactose, gelling agents, fluidizing agents, and preservatives, which in themselves are conventional.

The 4-O-β-D-galactopyranosyl-D-xylose or compositions or solutions that contain it are administered orally and lead to the existence of xylose in urine and this xylose that is spectrophotometrically analyzed, is used in a specific, routine, bloodless and simple manner for diagnostic evaluation of deficiencies of lactase activity.

EMBODIMENTS OF THE INVENTION

The invention will now be described on the basis of some examples that will illustrate with more detail some of the above-cited characteristics.

EXAMPLE 1

In order to determine the influence of the reaction temperature, the following test was carried out:
Samples of reaction mixtures comprised of
125 mg (500 mM) of D-xylose
25 mg (50 mM) of o-nitrophenyl E-D-galactopyranoside
1.75 ml of a reaction medium comprised
of an aqueous solution buffered to a pH of 7 (0.05 M KH$_2$PO$_4$/K$_2$HPO$_4$, 1 mM MgCl$_2$, 5 mM mercaptoethanol), were prepared and units of *E. coli* β-galactosidase enzyme were added to these samples in terms of the reaction temperatures applied, in accordance with the following table:

| reaction temperature (° C.) | added units of enzyme (u) |
| --- | --- |
| 45 | 1.6 |
| 37 | 1.6 |
| 25 | 1.6 |
| 5 | 10 |
| −5 | 20 |

The increases in the amount of enzyme were necessary in order to compensate the slowing down of the reaction produced by the drop of the reaction temperature. It should be indicated that it is possible to work at temperatures below the freezing point of water thanks to the cryoscopic drop that is produced in the reaction medium thanks to the high concentration of sugar in the samples.

The ratio between 4-, 2- and 3-O-β-D-galactopyranosyl-D-xylose was determined for each one of the samples and for each step of the process by gas chromatography by a chromatograph equipped with a flame ionization detector and a SE-54 capillary column 15 m long, with an inside diameter of 0.15 mm and a thickness of 0.3 μm. A nitrogen flow of 1 ml/min was used. The temperature program used was

| | |
| --- | --- |
| Initial temperature: | 160° C. |
| Initial time: | 2 min |
| Temperature increase: | 5° C./min |
| Final temperature: | 250° C. |

The samples were analyzed after trimethylsililation by means of the following protocol:

An aliquot (10 μl) was frozen at −170° C. and lyophilized until a dry residue was obtained, after which pyridine (25-μl) that contained as an internal reference benzyl β-D-xylopyranoside (10 mM) and N-trimethylsilimidazole (25 μl) was added to the dry residue and heating at 60° C. was continued for 30 minutes. The retaining times of the peaks assignable to the different disaccharides were the following:

| | |
|---|---|
| Benzyl β-D-xylopyranoside: | 12.04 min. |
| 2-O-β-D-galactopyranosyl-D-xylose: | 18.46 and 19.50 min. |
| 3-O-β-D-galactopyranosyl-D-xylose: | 18.30 min. |
| 4-O-β-D-galactopyranosyl-D-xylose: | 20.35 and 20.50 min. |

The following table reflects the proportions taken at the maximum formation of disaccharides, of 4-O-β-D-galactopyranosyl-D-xylose (=compound I) with respect to the sum of its regioisomers 2- and 3-O-β-D-galactopyranosyl-D-xylose that were obtained:

TABLE 1

| Temperature | Approximate reaction time (minutes) | Ratio of compound I/compounds II + III |
|---|---|---|
| 45 | 90 | 68:32 |
| 37 | 150 | 71:29 |
| 25 | 180 | 79:21 |
| 5 | 270 | 80:20 |
| −5 | 120 | 83:17 |

From the above table it is inferred that as the temperature dropped, there was an increase in the proportion of 4-O-β-D-galactopyranosyl-D-xylose.

EXAMPLE 2

In order to determine the influence of the pH on the reaction, the following samples were prepared:

| | |
|---|---|
| Gal-ONP (50 mM): | 25 mg |
| D-xylose (500 mM): | 125 mg |
| *E. coli* galactosidase | 1.6 u |
| Buffered aqueous solution (potassium phosphate 50 mM, 1 mM MgCl$_2$, 5 mM mercaptoethanol) at pH | |
| 8.5 | 1.6 ml |
| 7 | 1.6 ml |
| 5 | 1.6 ml | and they were reacted at 37° C.

The progress of the reaction was followed in the same way as described in example 1.

The following table reflects the proportions of 4-O-β-D-galactopyranosyl-D-xylose (=compound I) with respect to the sum of its regioisomers 2- and 3-O-β-D-galactopyranosyl-D-xylose that were obtained:

TABLE 2

| PH | Approximate reaction time (minutes) | Ratio of compound I/compounds II + III |
|---|---|---|
| 8.5 | 60 | 68:32 |
| 7 | 150 | 71:29 |
| 5 | 180 | 81:19 |

From the above table it is inferred that in a basic medium (pH=8.5), the proportion of compound I was lower than in a neutral medium (pH=7), detecting the highest proportion of compound I in an acid medium (pH=5).

EXAMPLE 3

In order to synthesize 4-O-β-D-galactopyranosyl-D-xylose, 6 g of o-nitrophenyl β-D-galactopyranoside (Gal-ONP) and 25 g of D-xylose were dissolved in 330 ml of water buffered to a pH of 7 (0.05 M KH$_2$PO$_4$/K$_2$HPO$_4$, 1 mM MgCl$_2$, 5 mM mercaptoethanol), 2 mg (640 u) of *E. coli* β-galactosidase enzyme were added and the solution thus obtained was subjected to incubation at 30° C. in an orbital stirrer until the Gal-ONP was practically consumed (approximately 4 hours). The follow-up of the reaction was carried out by thin layer chromatography (tlc) with isopropanol/NH$_3$ (30%)/H$_2$O=7.5/0.5/2.5 as eluent and taking as reference the following Rf values:

| | |
|---|---|
| Rf (Gal-ONP): | 0.58 |
| Rf (D-xylose): | 0.47 |
| Rf (4-O-β-D-galactopyranosyl-D-xylose): | 0.17 |
| Rf (2-O-β-D-galactopyranosyl-D-xylose + 3-O-β-D-galactopyranosyl-D-xylose): | 0.26 |

The reaction was stopped by heating in a water bath at 100° C. for 10 minutes and afterwards the o-nitrophenol formed was extracted with CH$_2$Cl$_2$. The aqueous solution was concentrated to dryness and the residue was acetylated in a conventional manner (acetic anhydride/pyridine=1:1, at room temperature, overnight and with magnetic stirring). Afterwards, the reaction mixture was concentrated and the pyridine and acetic anhydride residues were eliminated by successive additions and evaporations of toluene. The precipitated salts were filtered, the filtrate was concentrated to dryness and the residue was chromatographed in a silica gel column using a gradient of hexane/ethyl acetate in a ratio of 4:1-1:1 as the eluent. First acetylated D-xylose was eluted from the column and afterwards the mixture of acetylated disaccharides. Once the fractions that contained the mixture of disaccharides were concentrated, the residue was dissolved in MeOH, a solution of 1M MeONa/MeOH was added and the mixture thus obtained was stirred until deacetylation was complete (follow-up by tlc with isopropanol/NH$_3$/H$_2$O). The mixture was neutralized with AMBERLITE IR-120 (H$^+$) and concentrated to dryness. The mixture of free disaccharides was crystallized twice successively with MeOH/acetone, obtaining 1.07 g of pure 4-O-β-D-galactopyranosyl-D-xylose with a yield of 17% based on the initial Gal-ONP. (Melting point: 171-176°; $^1$HNMR (D$_2$O): δ 5.17 and 4.58 (2D, 1h, J. 3.8 and 7.8 Hz, H-1α and H-1β), 4.55 and 4.45 (2d, 1H, J 7.8 Hz, H-1'), 4.05 (dd, 1H, J 5.3 and 11.6 Hz, H-5e), 3.38 (dd, 1H, J 10.6 and 11.6 Hz), 3.25 (dd, 1H, J 7.8 and 9.4 Hz, H-2').

EXAMPLE 4

A column of active carbon/celite was prepared by dry mixing 200 g of activated carbon (DARCO G-60) and 200 g of celite and water was added until a homogeneous paste was formed. The paste was treated with 150 ml of HCl (35%) in order to deactivate the carbon, as well as to wash the residue of iron and alkaline ashes and afterwards this was washed with water until the washing water was neutral. Once washed, the paste was packed in a 5 cm (φ)×50 cm chromatography column and compacted.

In order to synthesize 4-O-β-D-galactopyranosyl-D-xylose, 5 g of o-nitrophenyl β-D-galactopyranoside (Gal-ONP)

and 25 g of D-xylose were dissolved in 330 ml of water buffered to a pH of 7 (0.05 M $KH_2PO_4/K_2HPO_4$, 1 mM $MgCl_2$, 5 mM mercaptoethanol), 2 mg (640 u) of *E. coli* β-galactosidase enzyme were added and the solution thus obtained was subjected to incubation at 37° C. in an orbital stirrer until the Gal-ONP was practically consumed (approximately 2 hours). Following the methodology put forth in example 3, the reaction was stopped by heating at 100° C. for 10 minutes and the ortho-nitrophenol formed was extracted with ethyl acetate. The aqueous solution was concentrated up to an approximate volume of 50 ml, filtered through glass-wool and passed through the active carbon/celite column. First of all, the excess D-xylose was eluted with water and afterwards, using a fractioned gradient of $EtOH/H_2O$ (2%-10% of EtOH) the mixture of disaccharides was collected. The enriched fractions in the 4-O-β-D-galactopyranosyl-D-xylose regioisomer were combined and concentrated to a reduced volume, after which acetone was added until turbidity appeared and the mixture thus obtained was left to stand cold. The 4-O-β-D-galactopyranosyl-D-xylose was crystallized in a pure form, obtaining 970 mg, namely, a yield of 19% based on the initial Gal-ONP, whose spectral data coincided with those given for the product obtained in accordance with example 3.

EXAMPLE 5

An active carbon/celite column was prepared by dry mixing 200 g of activated carbon (DARCO G-60) and 200 g of celite and water was added until a homogeneous paste was formed. The paste was treated with 150 ml of HCl (35%) in order to deactivate the carbon and to wash residues of iron and alkaline ashes and afterwards this was washed with water until the washing water was neutral. Once washed, the paste was packed in a 5 cm (ϕ)×50 cm chromatography column and compacted.

In order to synthesize 4-O-β-D-galactopyranosyl-D-xylose, 5 g of o-nitrophenyl β-D-galactopyranoside (Gal-ONP) and 25 g of D-xylose were dissolved in 330 ml of water buffered to a pH of 7 (0.05 M $KH_2PO_4/K_2HPO_4$, 1 mM $MgCl_2$, 5 mM mercaptoethanol), 2 mg (640 u) of *E. coli* β-galactosidase enzyme were added and the solution thus obtained was subjected to incubation at 37° C. in an orbital stirrer until the Gal-ONP was practically consumed (approximately 2 hours). Following the methodology put forth in example 3, the reaction was stopped by heating at 100° C. for 10 minutes and the ortho-nitrophenol formed was extracted with ethyl acetate. The aqueous solution was concentrated up to an approximate volume of 50 ml, filtered through glass wool and passed through the active carbon/celite column.

In order to crystallize the 4-O-β-D-galactopyranosyl-D-xylose, first of all, the excess D-xylose was eluted with water and afterwards, using a fractioned gradient of $EtOH/H_2O$ (2%-10% of EtOH) the mixture of disaccharides was collected. The enriched fractions in the 4-O-β-D-galactopyranosyl-D-xylose regioisomer were combined and concentrated to a reduced volume and dissolved in the minimum amount of water possible, after which acetone was added drop by drop until turbidity appeared and the mixture thus obtained was left at room temperature for two hours. After two hours, a check was made with a thin layer of the supernatant (transparent) that there was still an amount of uncrystallized 4-O-β-D-galactopyranosyl-D-xylose. Acetone was added again until there was turbidity and same was left to stand for another two hours. Finally, more acetone was added and the sample was stored in a refrigerator overnight and it was observed that the supernatant produced contained only a minimum amount of 4-O-β-D-galactopyranosyl-D-xylose. The crystals of 4-O-β-D-galactopyranosyl-D-xylose were filtered and washed with acetone.

The 4-O-β-D-galactopyranosyl-D-xylose was obtained in a pure form, obtaining 1,557 mg, in other words, a yield of 30% based on the initial Gal-ONP, whose spectral data coincide with those given regarding the product obtained in accordance with example 3.

EXAMPLE 6

An active carbon/celite column was prepared by dry mixing 200 g of activated carbon (DARCO G-60) and 200 g of celite and water was added until a homogenous paste was formed. The paste was treated with 150 ml of HCl (35%) in order to deactivate the carbon and wash the residues of iron and alkaline ashes and afterwards it was washed with water until the washing water was neutral. Once washed, the paste was packed in a 5 cm ϕ×50 cm chromatography column and compacted.

In order to synthesize 4-O-β-D-galactopyranosyl-D-xylose, 5 g of o-nitrophenyl β-D-galactopyranoside (Gal-ONP) and 25 g of D-xylose were dissolved in 330 ml of water buffered to a pH of 6.8 (0.05 M $KH_2PO_4/K_2HPO_4$, 1 mM $MgCl_2$ 5 mM mercaptoethanol), 70 units of *Kluyveramyces lactis* (MAXILACT®) β-galactosidase enzyme were added and the solution thus obtained was subjected to incubation at 37° C. in an orbital stirrer until the Gal-ONP was practically consumed (approximately 2 hours). The reaction was followed by thin layer chromatography with isopropanol/$NH_3$ (30%)/$H_2O$ (7.5/0.5/2.5) resulting in the following Rf values:

| | |
|---|---|
| Rf (Gal-ONP): | 0.58 |
| Rf (D-xylose): | 0.47 |
| Rf (4-O-β-D-galactopyranosyl-D-xylose): | 0.17 |
| Rf (2-O-β-D-galactopyranosyl-D-xylose + 3-O-β-D-galactopyranosyl-D-xylose): | 0.26 |

Following the methodology put forth in example 4, the reaction was stopped by heating at 100° C. for 10 minutes and the ortho-nitrophenol formed was extracted with ethyl acetate and was filtered to eliminate the enzyme residues. The aqueous solution was concentrated under a vacuum up to an approximate volume of 45 ml and passed through the active carbon/celite column. First of all, the excess D-xylose was eluted with water and afterwards, using a fractioned gradient of $EtOH/H_2O$ (2%-10% of EtOH) the mixture of disaccharides was collected. The enriched fractions in the 4-O-β-D-galactopyranosyl-D-xylose regioisomer were combined and concentrated to a reduced volume, after which acetone was added until turbidity appeared and the mixture thus obtained was left to stand cold. The crystallized 4-O-β-D-galactopyranosyl-D-xylose, was filtered through a filtering plate, obtaining 817 mg, namely, a yield of 16% based on the initial Gal-ONP.

EXAMPLE 7

An active carbon/celite column was prepared by dry mixing 200 g of activated carbon (DARCO G-60) and 200 g of celite and water was added until a homogenous paste was formed. The paste was treated with 150 ml of HCl (35%) in order to deactivate the carbon and wash the residues of iron and alkaline ashes and afterwards it was washed with water until the washing water was neutral. Once washed, the paste was packed in a 5 cm φ×50 cm chromatography column and compacted.

In order to synthesize 4-O-β-D-galactopyranosyl-D-xylose, 5 g of o-nitrophenyl β-D-galactopyranoside (Gal-ONP) and 25 g of D-xylose were dissolved in 330 ml of water buffered to a pH of 7 (0.05 M $KH_2PO_4/K_2HPO_4$, 1 mM $MgCl_2$, 5 mM mercaptoethanol), 80 units of *E. coli* β-galactosidase enzyme were added and the solution thus obtained was subjected to incubation at 37° C. in an orbital stirrer for 24 hours. The reaction was followed by thin layer chromatography with isopropanol/$NH_3$(30%)/$H_2O$ (7.5/0.5/2.5) resulting in the following Rf values:

| | |
|---|---|
| Rf (Gal-ONP): | 0.58 |
| Rf (D-xylose): | 0.47 |
| Rf (4-O-β-D-galactopyranosyl-D-xylose): | 0.17 |
| Rf (2-O-β-D-galactopyranosyl-D-xylose + 3-O-β-D-galactopyranosyl-D-xylose): | 0.26 |

Following the methodology put forth in example 3, the reaction was stopped by heating at 100° C. for 10 minutes and the ortho-nitrophenol formed was extracted with ethyl acetate and was filtered to eliminate the enzyme residue. The aqueous solution was concentrated under a vacuum up to an approximate volume of 70 ml and the concentrated solution was eluted through a active carbon/celite column. First of all, it was eluted with isopropanol/water (2%) and 1.3 liters were collected. Afterwards 4% fractions were collected up to 2.6 liters, using a total volume of 3.9 liters.

The enriched fractions in the 4-O-β-D-galactopyranosyl-D-xylose regioisomer were combined and concentrated to a reduced volume, after which acetone was added until turbidity appeared and the mixture thus obtained was left to stand cold. The crystallized 4-O-β-D-galactopyranosyl-D-xylose was filtered through a filtering plate, obtaining 1,213 mg, namely, a yield of 24% based on the initial Gal-ONP.

EXAMPLE 8

An active carbon/celite column was prepared by dry mixing 24 g of activated carbon (DARCO G-60) and 24 g of celite and water was added until a homogenous paste was formed. The paste was treated with 18 ml of HCl (35%) in order to deactivate the carbon and wash the residues of iron and alkaline ashes and afterwards it was washed with water until the washing water was neutral. Once washed, the paste was packed in a chromatography column and compacted.

In order to synthesize 4-O-β-D-galactopyranosyl-D-xylose, 5 g of o-nitrophenyl β-D-galactopyranoside (Gal-ONP) and 25 g of D-xylose were dissolved in 330 ml of water buffered to a pH of 7 (0.05 M $KH_2PO_4/K_2HPO_4$, 1 mM $MgCl_2$, 5 mM mercaptoethanol), 80 units of *E. coli* β-galactosidase enzyme were added and the solution thus obtained was subjected to incubation at 37° C. in an orbital stirrer until the Gal-ONP was practically consumed (24 hours). The reaction was followed by thin layer chromatography with isopropanol/$NH_3$(30%)/$H_2O$ (7.5/0.5/2.5) in a way similar to the one indicated in example 7. Following the methodology put forth in example 3, the reaction was stopped by heating at 100° C. for 10 minutes, it was allowed to cool and the ortho-nitrophenol formed was extracted with ethyl acetate. Celite (40 g) was added to the aqueous solution and the mixture was concentrated to dryness. The solid residue was subjected to solid-liquid extraction using a Soxhlet extractor equipped with a cellulose cartridge and using ethyl acetate (500 ml) as the solvent. After 23 hours, the resulting solid was washed with water (3×40 ml) and the aqueous solution was eluted through an active carbon-celite column. First of all, it was eluted with isopropanol/water (2%) and afterwards with isopropanol/water (4%), using a total volume of eluent of 400 ml. The enriched fractions in the 4-O-β-D-galactopyranosyl-D-xylose regioisomer were combined and concentrated to dryness. The residue was crystallized from acetone-water in a way similar to the one described in example 7, obtaining 0.44 g of pure crystalline disaccharide.

EXAMPLE 9

In order to synthesize 4-O-β-D-galactopyranosyl-D-xylose, 4.12 g of o-nitrophenyl β-D-galactopyranoside (Gal-ONP) and 20.6 g of D-xylose were dissolved in 272 ml of water buffered to a pH of 7 (0.05 M $KH_2PO_4/K_2HPO_4$, 1 mM $MgCl_2$, 5 mM mercaptoethanol), 66 units of *E. coli* β-galactosidase enzyme were added and the solution thus obtained was subjected to incubation at 37° C. in an orbital stirrer until the Gal-ONP was practically consumed (21 hours). The reaction was stopped by cooling to 0° C. and the o-nitrophenol was filtered as a solid. 60 g of active carbon were added to the filtrate and the resulting mixture was stirred for 30 min. By means of tlc of the supernatant, the absence of disaccharide in the solution was observed, since same was adsorbed on the active carbon. The mixture was filtered and the active carbon solid was washed with water (400 ml), 2% isopropanol (100 ml), 4% isopropanol (200 ml) and 6% isopropanol (200 ml). The fractions that contained disaccharide 4-O-β-D-galactopyranosyl-D-xylose were concentrated and the residue (2.38 g) was crystallized from acetone-water, obtaining 1.55 g of a solid that was crystallized again from the same mixture of solvents in a way similar to the one used in example 7. 1.32 g of pure disaccharide (32%) were obtained.

The invention claimed is:

1. A method for producing 4-O-β-D-galactopyranosyl-D-xylose enzymatically in a ratio of at least 68:32 by weight of 4-O-β-D-galactopyranosyl-D-xylose to the combined sum of 2-O-β-D-galactopyranosyl-D-xylose and 3-O-β-D-galactopyranosyl-D-xylose comprising the following steps:
   (i) preparing a first reaction mixture of 2-20% by weight of D-xylose, 0.5 to 5% by weight of a β-D-galactopyranoside substrate, and 75-97.5% by weight of a reaction medium that comprises buffered water at a pH between 5.0 and 9.0; adding 10 to 1,000 units of a β-D-galactosidase enzyme, per gram of β-D-galactopyranoside, to the first reaction mixture; and obtaining a second reaction mixture;
   (ii) subjecting the second reaction mixture to a reaction at a temperature comprised between a temperature higher than the freezing point of the second reaction mixture and 45° C., for 2 to 48 hours, in order to form disaccharides in the second reaction mixture;
   (iii) stopping the reaction when the disaccharides have been formed in the desired amount, by means of a treatment selected from the group consisting of:
      a) deactivation of β-D-galactosidase by freezing the second reaction mixture at a temperature between −20° C. and −170° C.,
      b) deactivation of β-D-galactosidase by heating the second reaction mixture at a temperature between 95° C. and 110° C. and
      c) separation of β-D-galactosidase from the second reaction mixture by ultrafiltration; obtaining a third reaction mixture;

(iv) separating an aglyconic fragment of the β-D-galactopyranoside substrate used in the first step from the third reaction mixture by extraction or filtration; obtaining a fourth reaction mixture;

(v) isolating fractions that contain 4-O-β-D-galactopyranosyl-D-xylose by a method selected from the group consisting of addition of celite to the fourth reaction mixture, followed by solid liquid extraction with a solvent and elution with a first eluent in a column wherein the first eluent is a mixture of water/isopropanol that contains 1 to 10% (v/v) of isopropanol; and directly adding active carbon to the fourth reaction mixture followed by filtration and elution with a second eluent;

(vi) crystallizing the fractions that contain 4-O-β-D-galactopyranosyl-D-xylose in a crystallization mixture selected from the group consisting of mixtures of acetone/methanol in a ratio between 5/1 to 20/1 and mixtures of acetone/water in a ratio between 5/1 to 20/1.

2. The method according to claim 1, wherein the fourth reaction mixture is concentrated before being subjected to elution in the column.

3. The method according to claim 1, wherein the mixture of acetone/methanol has a ratio of 10/1.

4. The method according to claim 1, wherein the mixture of acetone/water has a ratio of 10/1.

5. The method according to claim 1, wherein the mixture of water/isopropanol contains 2% (v/v) of isopropanol.

6. The method according to claim 1, wherein step (v) consists of adding celite to the fourth reaction mixture and concentrating to dryness, followed by solid-liquid extraction with an organic solvent in a Soxhlet extractor that has a cartridge made out of a material compatible with said solvent, and eluting with a first eluent in a column selected from the group consisting of filtration columns with cross-linked dextrane polymer fillers, filtration columns with acrylamide polymer fillers, filtration columns of active carbon and active carbon-celite columns.

7. The method according to claim 6, wherein the solvent is ethyl acetate.

8. The method according to claim 6, wherein the solvent is used in an amount between 10 ml and 25 ml per gram of initial xylose.

9. The method according to claim 6, wherein the celite is used in an amount between 1 g and 2 g per gram of initial xylose.

10. The method according to claim 6, wherein the column is of active carbon-celite wherein the carbon is deactivated by adding 35% hydrochloric acid.

11. The method according to claim 10, wherein the celite is used in an amount between 0.5 g and 2 g of celite per gram of initial xylose.

12. The method according to claim 10, wherein the active carbon is used in an amount between 0.5 g and 2 g of active carbon per gram of initial xylose.

13. The method according to claim 6, wherein said first eluent is used in an amount between 5 ml and 25 ml per gram of initial xylose.

14. The method according to claim 10, wherein the hydrochloric acid is used in an amount between 0.5 ml and 1.5 ml per gram of initial xylose.

15. The method according to claim 1, wherein in step (v), the fourth reaction mixture is subjected to direct addition of at least a second eluent on the active carbon wherein the 4-O-β-D-galactopyranosyl-D-xylose is adsorbed on the active carbon and the second eluent is water followed by diluted isopropanol with a growing proportion in volume of isopropanol in successive steps.

16. The method according to claim 15, wherein the proportion in volume of isopropanol is between 1% and 3% in a first step, between 3% and 5% in a second step and between 5% and 7% in a third step.

17. The method according to claim 15, wherein the active carbon is used in an amount between 2 g and 4 g of active carbon per gram of initial xylose.

18. The method according to claim 15, wherein the second eluent is used in a total amount between 30 ml and 50 ml of second eluent per gram of initial xylose.

19. The method according to claim 1, wherein the reaction is slowed by cooling the second reaction mixture at 0° C.

20. The method according to claim 1, wherein the fourth reaction mixture is obtained by separating the aglyconic fragment from the β-D-galactopyranoside substrate by means of filtration.

21. The method according to claim 1, wherein the proportion of D-xylose in the second reaction mixture is 7.5% by weight.

22. The method according to claim 1, wherein the proportion of β-D-galactopyranoside in the second reaction mixture is 1.5% by weight.

23. The method according to claim 1, wherein 20 units of β-D-galactosidase per gram of β-D-galactopyranoside are added.

24. The method according to claim 1, wherein the reaction medium also comprises at least a cosolvent medium selected from the group consisting of dimethylsulfoxide, dimethylformamide, dioxane and mixtures thereof.

25. The method according to claim 24, wherein the reaction medium comprises 20% by weight of the cosolvent medium.

26. The method according to claim 1, wherein the reaction is carried out at a constant temperature.

27. The method according to claim 1, wherein the reaction temperature is from −5° C. to 40° C.

28. The method according to claim 1, wherein the reaction temperature is higher than the freezing temperature of the second mixture and lower than 0° C.

29. The method according to claim 1, wherein the reaction temperature is −5° C.

30. The method according to claim 1, wherein the reaction temperature is room temperature.

31. The method according to claim 1, wherein the reaction medium is buffered to a pH of 7.

32. The method according to claim 1, wherein in step (iii), the reaction is stopped by freezing the second reaction mixture at a temperature of −78° C.

33. The method according to claim 1, wherein in step (iii), the reaction is stopped by heating the second reaction mixture up to a temperature of 100° C.

34. The method according to claim 1, wherein in step (iii), the reaction is stopped by separating the β-D-galactosidase by ultrafiltration.

35. The method according to claim 1, wherein the β-D-galactopiranoside substrate is selected from the group consisting of o-nitrophenyl β-D-galactopiranoside and lactose.

36. The method according to claim 1, wherein the β-D-galactosidase enzyme is *E. coli* β-D-galactosidase.

37. The method according to claim 1, wherein the β-D-galactosidase enzyme is *Kluyveramyces lactis* β-D-galactosidase.

* * * * *